(12) United States Patent
Raczek et al.

(10) Patent No.: US 6,652,921 B2
(45) Date of Patent: *Nov. 25, 2003

(54) WOOD CONTAINING FIXED SORBIC ACID OR SORBIC ACID SALTS

(75) Inventors: Nico N. Raczek, Kelkheim (DE); Katrin Saelzer, Gross-Krotzenburg (DE)

(73) Assignee: Nutrinova Nutrition Specialties & Food Ingredients GmbH, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/005,782

(22) Filed: Nov. 8, 2001

(65) Prior Publication Data

US 2002/0110677 A1 Aug. 15, 2002

(30) Foreign Application Priority Data

Dec. 16, 2000 (DE) .......................................... 100 62 984

(51) Int. Cl.⁷ .......................... B05D 1/18; A61K 31/19; C07C 57/10; A01N 47/10
(52) U.S. Cl. ...................... 427/440; 514/557; 562/601; 504/157
(58) Field of Search ............................ 514/557; 512/5; 562/601; 427/440, 441; 504/157

(56) References Cited

U.S. PATENT DOCUMENTS

| 4,303,668 A | * | 12/1981 | Hasegawa et al. | .......... 424/279 |
| 5,530,024 A | * | 6/1996 | Oppong et al. | ............. 514/515 |
| 5,880,143 A | * | 3/1999 | Goettsche et al. | .......... 514/383 |
| 2001/0018454 A1 | * | 8/2001 | Wetzel | ........................ 514/557 |

FOREIGN PATENT DOCUMENTS

| DE | 3609317 | * | 9/1987 |
| WO | WO 96/11572 A1 | | 4/1996 |

OTHER PUBLICATIONS

USP Dictionary of USAN and International Drug Names 1998. U.S. Pharmacopeia, Rockville MD. p. 35 (1998).*

* cited by examiner

Primary Examiner—Mukund J. Shah
Assistant Examiner—Zachary C. Tucker
(74) Attorney, Agent, or Firm—ProPat, L.L.C.

(57) ABSTRACT

The present invention relates to wood which contains a sorbic acid store and to processes for producing the sorbic acid store in the wood or on the surface of the wood. The present invention also relates to a process for using sorbic acid and its salts for protecting wood from microbially induced degradation.

17 Claims, No Drawings

WOOD CONTAINING FIXED SORBIC ACID OR SORBIC ACID SALTS

BACKGROUND OF THE INVENTION

1. Field of the Invention

The present invention relates to wood which contains a sorbic acid store, and to processes for producing the sorbic acid store in the wood or on the surface of the wood. The present invention also relates to a process for using sorbic acid and its salts for protecting wood from microbially induced degradation. This relates in particular to wood that is subject to particular climatic conditions; wood which can come into contact with foods, food-contact articles, feeds, petfood, cosmetics, food wastes or is used in the domestic exterior or living area. This invention relates in particular to the production of a store in the wood by permanent fixing of the sorbic acid in the wood and thus ensures a long-lasting action. In addition to the industrial use in processing and handling wood, use in the artisanal sector is also possible.

2. Description of the Related Art

"Sorbates" is taken to mean hereinafter sorbic acid and its salts. "Wood" is taken to mean hereinafter all of the long lasting tissue which is delimited in wood from the cambium of the plants, independent of the degree of lignification. Wood does not include pith or bark.

Wood, like all organic materials, is subject to microbially induced degradation. In addition to Basidiomycetes (stalk fungi) molds, yeasts and also bacteria also contribute to this. In the timber industry a great variety of wood preservatives are used.

Frequently the constituents of these wood preservatives are substances which are associated with a considerable health risk, for example fluorine compounds such as ammonium hydrogen fluoride, copper hexafluorosilicate or potassium hydrogen fluoride, arsenic compounds such as arsenic pentoxide, boron compounds such as boric acid or polyboron, or copper compounds such as copper sulfate. Frequently used chromium compounds such as potassium chromate or ammonium dichromate, however, are not biocides in the true sense, since these serve for fixing the biocides in the wood.

A disadvantage of said wood preservatives is that according to the German Dangerous Substances Ordinance, they must be classified as toxic or at least hazardous to health. Many of said wood preservatives are odor-neutral, so that their presence cannot thus be noticed. In many cases the consumers or users of a wood treated in this manner are also accustomed to its altered appearance (e.g. green discoloration) so that they do not notice treatment with a wood preservative. Despite the necessary industrial safety precautions when such wood preservatives are used in the industrial sector, the user of wood treated in this manner frequently is not informed about the possible risks to health of direct contact with the wood treated in this manner. In the case of long-lasting direct contact with this wood, the risk of later damage to health cannot be excluded.

In contrast to the use of such wood preservatives in the industrial sector, artisanal use in the house and home sector is therefore a problem.

Particularly strict guidelines must be applied, in particular for wood treated with wood preservatives which can come into contact with food, food-contact articles, feeds, petfood, cosmetics or food wastes. In this case there is also the possibility of direct transfer to the foods. Such a transfer must always be avoided in the case of substances which are not suitable for consumption or are even toxic, in order to exclude health risks.

Preservatives which are used to preserve various foods have also been tested for their applicability to preserving wood, in particular in the form of derivatives which are not used as such for food preservation. The water-insoluble zinc salt of sorbic acid has been described, for example, as inactive (Holzforschung 17, 97 (1963)). Treatment of bamboo with the commercially unavailable sodium sorbate generally showed, even after a few days, growth of fungi and poorer results than the dehydroacetic acid tested as an alternative. Sodium sorbate was only active in these studies at a pH of 3.0 which is unusual in practice (Hakko Kogaku Zasshi 37, 19 (1959)).

Food preservatives and their derivatives are not used as wood preservatives in practice, since they have hitherto been considered as insufficiently active. In contrast to the wood preservatives used in industry, the preservatives used in food processing are, however, safe for health, so that the transfer of residues to food packaging would be more tolerable than with industrial wood preservatives. In addition they are odor-neutral, so that they give rise to no impairment of food odor. This applies very particularly to sorbic acid which is structurally closely related to the fatty acids occurring in food fats and is degraded in the same manner as these fatty acids in the metabolism of the organism.

Sorbic acid and in particular its water-soluble salts are, in contrast to previous assumptions, absolutely in the position to protect wood and wood articles from wood-damaging fungi for a relatively long time. This protective action is achieved, although reference is generally made to the fact that sorbic acid and its salts are only active at an acidic pH of the material to be preserved (see, for example: Handbuch Lebensmittelzusatzstoffe [Handbook of food additives], Section BII-1.2, p. 3, 1997).

Sorbic acid (trans, trans-2,4-hexadienoic acid) is a colorless solid compound which dissolves only sparingly in cold water. The solubility in liquid alcohols is good in contrast. Potassium sorbate is a virtually colorless compound which dissolves very readily in water. Sorbic acid and its salts have a very good microbistatic, antimycotic action. At the same time, sorbic acid, as an unsaturated fatty acid, is virtually nontoxic, which very extensive data verify. Sorbic acid and its salts are accordingly permitted for food use by international committees and permitted worldwide as a preservative for direct addition to foods. The internationally established tolerable daily dose for humans of up to 25 mg/kg of body weight corresponds to a tolerable consumption by adults of up to 1.5 g per day (at a mean body weight of 60 kg).

When sorbic acid and its salts are used it is necessary to achieve a sufficiently high concentration at the wood surface and in its edge areas. Timber is generally never used completely dry and it has a residual moisture content adapted to its surroundings. Before a treatment with wood preservative, timbers are therefore generally dried. Remaining water is incorporated into the cell walls and therefore does not hinder the penetration of a sorbate solution into the wood capillaries. A dipping or spray treatment permits amounts of sorbate sufficient for surface treatment to penetrate into the wood, even with air-dry timber.

Depending on the moisture content, sorbic acid can, however, slowly diffuse further into the cell walls and also through them. The more moisture is present already in the wood, the easier and deeper is the distribution of sorbic acid into the deeper layers of the wood. In the case of intensive diffusion into the depth of the wood, in extreme cases this can lead to the fact that the concentration of sorbates in the impregnated wood area is so low that sufficient wood preservation action is no longer achieved. If timber which has been treated with sorbates is exposed to water for some time, for example rain or water condensing from moist air, the sorbates can also be washed out again. As a result the protective action is decreased, or it is even completely lost.

The purpose of the invention is, by modifying the sorbic acid treatment, to prevent the sorbic acid or salts of sorbic acid from diffusing out or washing out. The object of the present invention is therefore, when sorbates are used as wood preservatives, to ensure that sufficient concentrations active against fungi remain in the outer layers of the wood.

SUMMARY OF THE INVENTION

Surprisingly, it has now been found that by generating poorly soluble stable sorbic acid salts directly in the wood, this object was achieved. Silver, copper, mercury, lead, aluminum, chromium, iron or tin salts of sorbic acid, but preferably calcium sorbate and magnesium sorbate, add in a relatively fixed manner to the wood cells and thus form a store which firstly prevents the diffusion of the sorbates into deeper wood layers and secondly prevents washing out. Stored forms of sorbic acid in wood, however, can also be achieved in the wood by displacing water by oil, or by sorbic acid itself, with organic or inorganic acids being used.

The invention therefore relates to wood containing a sorbic acid store.

The invention also relates to a wood in which the sorbic acid store is a silver, copper, mercury, lead, aluminum, chromium, iron, tin, calcium or magnesium salt of sorbic acid or is a mixture of one or more of said salts. Preference is given to a calcium salt or magnesium salt of sorbic acid.

The invention also relates to a wood in which the sorbic acid store consists of an organic or inorganic acid and sorbic acid. Preference is given to organic acids such as citric acid, fumaric acid or lactic acid.

The invention further relates to a wood in which the sorbic acid store consists of an oil and sorbic acid and/or one or more salts of sorbic acid.

Preferably, an oil from oilseeds is used, in which the sorbic acid and/or one or more salts of sorbic acid are present in dissolved form.

Suitable oils are, for example, olive oil, oil palm oil, avocado oil, rapeseed oil, linseed oil, flax oil, soybean oil, cottonseed oil, peanut oil, sunflower seed oil, pumpkin seed oil, castor bean oil, poppyseed oil, sesame oil, coconut oil, cocoa bean oil, almond oil, walnut oil, hazelnut oil, grapeseed oil, corn oil or mixtures of said oils.

The invention further relates to a process for producing a sorbic acid store, which comprises a) treating wood with a solution containing one or more water-soluble silver, copper, mercury, lead, aluminum, chromium, iron, tin, calcium or magnesium salts, b) drying the wood thus treated and c) treating the dried wood with sorbic acid and/or one or more salts of sorbic acid.

DETAILED DESCRIPTION OF THE INVENTION

In the process of the invention, a procedure is followed such that firstly an aqueous solution of a silver, copper, mercury, lead, aluminum, chromium, iron, tin, calcium or magnesium salt is prepared. This solution is termed hereinafter fixing solution. Suitable salts are, for example, $CaCl_2$, $MgSO_4$, $CaHPO_4$, $Ca(OH)_2$, $MgCl_2$, $FeCl_3$, $FeSO_4$, $AlCl_3$, $Al(H_2PO_4)_3$, $Pb(NO_3)_2$ or $Pb(CH_3COO)_2$. Preferably, calcium salts or magnesium salts are used in the fixing solution here. Mixtures of the different salts can also be prepared. The wood is then treated with the fixing solution. All processes are suitable by which the surface of the wood or the wooden articles can be wetted uniformly with the fixing solution, that is, for example, dipping, spraying, coating and others. The concentration of salts in the fixing solution is adapted to the intended treatment process. The concentrations can be varied in principle in wide limits and are limited upwardly only by the solubility limit, and downwardly by the insufficient concentration to produce the corresponding sorbate. Suitable concentrations of salts in the fixing solution are preferably 0.1–10.0% by weight, particularly preferably 1.0–5.0% by weight.

For a particularly protective action, instead of a simple dipping treatment, pressure impregnation or impregnation after preceding evacuation can occur, in each case using said fixing solution.

After treatment with the fixing solution, generally simple drying in dry air of the wood thus treated is sufficient in order to prepare the wood for the next process step. Alternatively, obviously, accelerated drying in heated rooms or chambers or in a hot or dry air stream is also possible.

The treatment with sorbic acid and/or one or more salts of sorbic acid then follows. Suitable processes are all above-mentioned processes by which the surface of the wood or the wooden articles can be uniformly wetted with sorbic acid. The concentrations of sorbic acid and/or salts of sorbic acid are adapted to the intended treatment process. They can vary in principle in wide ranges and are only limited upwardly by the solubility limit and downwardly by the protective action which is only low at insufficient concentrations. Usually, solutions of the salts in water or alcohols such as branched or unbranched $C_1$–$C_4$-alkanols and/or $C_2$–$C_4$-alkanediols or mixtures of these alcohols with water, in particular aqueous propylene glycol at preferred concentrations in the range from 5% by weight to 50% by weight, in particular in the range of 10% by weight to 40% by weight, are used.

For particularly intensive protective action, instead of a simple dipping treatment pressure impregnation or impregnation after preceding evacuation can also occur, in each case with solutions of sorbic acid and/or sorbic acid salts in water or mixtures of water and propylene glycol.

After treatment with sorbic acid, generally, simple drying in dry air is sufficient to achieve the desired protective action. Alternatively, obviously, accelerated drying in heated rooms or chambers or in a warm or dry air stream is also possible.

The process steps a) and c) can also be exchanged. However, then higher concentrations of the salts in the fixing solution will be required.

The sorbates fixed in this manner add in a relatively fixed manner to the wood cells and thus form a store which firstly prevents the diffusion of the sorbates into deeper wood layers and secondly prevents them washing out. Low pHs (in particular pH 1 to pH 4) favorably affect the fixing rate. It can also be considerably increased by short-time subsequent hot-stream treatment.

The treatment is preferably performed on the wooden parts intended for further processing, so that the entire surface comes uniformly into contact with the fixing solution and the sorbic acid and/or the salts of sorbic acid.

However, it can also be performed on finished wooden articles, if the shape permits contact with the entire surface with the solutions.

The invention also relates to a process for producing a sorbic acid store, which comprises
- a) treating wood with a solution comprising one or more organic or inorganic acids different from sorbic acid,
- b) drying the wood thus treated and
- c) treating the dried wood with sorbic acid and/or one or more salts of sorbic acid.

Examples of usable organic acids are formic acid, acetic acid, propionic acid, citric acid, fumaric acid or lactic acid. Preference is given to citric acid, fumaric acid and lactic acid. Inorganic acids which can be used are, for example, hydrochloric, sulfuric or phosphoric acid. The acids are preferably used at concentrations of 0.1–10.0% by weight, particularly preferably 1.0–5.0% by weight (based on the solution). Sorbic acid or its salts are expediently used at concentrations of 1 to 10% by weight.

This inventive process enables sorbic acid to be fixed if flammable solvents cannot be employed. In this case organic and/or inorganic acids are used which can be used together with aqueous solutions of salts of sorbic acid in the manner described for the fixing solution for pretreatment or post-treatment of the wood. In this case sorbic acid precipitates out of the sorbic acid solution used or of the salt of sorbic acid in the treated wood. The abovementioned methods of treating the wood mentioned for the fixing solution are used for introducing the acids into the wood.

Process steps a) and c) can also be exchanged. However, higher concentrations of the acids will then be required.

The invention further relates to a process for producing a sorbic acid store, wherein wood is treated with an oil containing sorbic acid and/or one or more salts of sorbic acid.

Suitable oils are, for example, oils from oilseeds in which the sorbic acid and/or one or more salts of sorbic acid are present in the dissolved form.

Suitable oils are olive oil, oil palm oil, avocado oil, rapeseed oil, linseed oil, flax oil, soybean oil, cottonseed oil, peanut oil, sunflower seed oil, pumpkin seed oil, castor bean oil, poppyseed oil, sesame oil, coconut oil, cocoa bean oil, almond oil, walnut oil, hazelnut oil, grapeseed oil, corn oil or mixtures of said oils.

The concentration of sorbic acid or sorbic acid salts is from 0.1% by weight to 1% by weight.

The abovementioned methods of treating the wood already mentioned for the fixing solution are used for introducing or applying the oil into the wood.

The invention also relates to the use of a sorbic acid store for protecting wood from microbially induced degradation, in particular for degradation by fungi such as Basidiomycetes, molds or yeasts.

The invention is explained by the following examples:

EXAMPLE 1

Sprucewood boards were set to a moisture content of 9.3% by weight, 18.8% by weight and 19.4% by weight by storage at a defined ambient moisture. The moisture was determined gravimetrically.

Two process variants were used:

Variant A

The treatment was performed using an aqueous solution containing 5% by weight of a fixing agent. The wood was dipped into the fixing solution for 15 min. The wood was then dried for approximately 5–10 min. The wood thus treated was then immersed into a solution of potassium sorbate in water (5% by weight) for 15 min.

Variant B

In variant B, the sequence of fixing solution and potassium sorbate solution was interchanged.

The sorbic acid contents were then measured in a layer about 2 mm deep. The following results were obtained:

| | Variant A | | |
|---|---|---|---|
| | Sorbic acid concentrations in g/m² of wood surface | | |
| | Moisture (%) | | |
| | 9.3% | 18.8% | 19.4% |
| Fixing agent | Amount of sorbic acid (g/m²) | | |
| CaCl₂ | 24 | 34 | 31 |
| MgSO₄ | 23 | 23 | 23 |
| Citric acid | 37 | 40 | 38 |
| Lactic acid | 25 | 28 | 33 |

| | Variant B | | |
|---|---|---|---|
| | Amount of sorbic acid in g/m² of wood surface | | |
| | Moisture (%) | | |
| | 9.3% | 18.8% | 19.4% |
| Fixing agent | Sorbic acid (g/m²) | | |
| CaCl₂ | 13 | 14 | 11 |
| MgSO₄ | 14 | — | — |
| Citric acid | 13 | 17 | 18 |
| Lactic acid | 9 | 12 | 14 |

It was found that in the case of prior use of fixing agent solutions, significantly higher amounts of sorbic acid or sorbate can be applied to the wood.

We claim:

1. A wood which contains a sorbic acid store, wherein the sorbic acid store is either a calcium salt or magnesium salt of sorbic acid or sorbic acid and another acid selected from one or more of formic acid, acetic acid, propionic acid, citric acid, fumaric acid, lactic acid, hydrochloric acid, sulfuric acid and phosphoric acid or an oil and one or more of sorbic acid and a salt of sorbic acid and wherein the wood is essentially free of other added active components.

2. The wood as claimed in claim 1, wherein the oil is selected from one or more of olive oil, palm oil, avocado oil, rapeseed oil, linseed oil, flax oil, soybean oil, cottonseed oil, peanut oil, sunflower seed oil, pumpkin seed oil, castor bean oil, poppyseed oil, sesame oil, coconut oil, cocoa bean oil, almond oil, walnut oil, hazelnut oil, corn oil and grapeseed oil.

3. A process for producing a wood as claimed in claim 1, which comprises
   - a) treating wood with a solution containing one or more water-soluble calcium or magnesium salts,
   - b) drying the wood thus treated and
   - c) treating the dried wood with one or more of sorbic acid and a salts of sorbic acid.

4. The process as claimed in claim 3, wherein the water-soluble calcium or magnesium salts are selected from one or more of $CaCl_2$, $MgSO_4$, $CaHPO_4$, $Ca(OH)_2$ and $MgCl_2$.

5. The process as claimed in claim 3, wherein the dried wood is treated with a solution comprising one or more salts of sorbic acid in water or alcohol or mixtures of alcohol with water.

6. The process as claimed in claim 5, wherein the solution comprises propylene glycol and water.

7. The process as claimed in claim 3, wherein one or more of the sorbic acid salts is used at a concentration of from 5% by weight to 50% by weight, in particular from 10% by weight to 40% by weight.

8. A process for producing a wood as claimed in claim 1, which comprises
   a) treating wood with a solution comprising one or more acids selected from formic acid, acetic acid, propionic acid, citric acid, fumaric acid, lactic acid, hydrochloric acid, sulfuric acid and phosphoric acid,
   b) drying the wood thus treated and
   c) treating the dried wood with one or more of sorbic acid and a salt of sorbic acid.

9. A process for producing a wood as claimed in claim 1, wherein wood is treated with an oil comprising one or more of sorbic acid and a salt of sorbic acid.

10. The process as claimed in claim 9, wherein the oil is selected from one or more oils of olives, palm, avocado, rapeseed, linseed, flax, soybean, cottonseed, peanut, sunflower seed, pumpkin seed, castor bean, poppy, sesame, coconut, cocoa bean, almond, walnut, hazelnut, grapeseed and corn.

11. The process as claimed in claim 9, wherein the concentration of sorbic acid or sorbic acid salts is 0.1% by weight to 1% by weight.

12. A method for protecting wood from microbial induced degradation which method comprises treating wood with a sorbic acid store, wherein the sorbic acid store is either a calcium salt or magnesium salt of sorbic acid or sorbic acid and another acid selected from one or more of formic acid, acetic acid, propionic acid, citric acid, fumaric acid, lactic acid, hydrochloric acid, sulfuric acid and phosphoric acid or an oil and one or more of sorbic acid and a salt of sorbic acid and wherein the sorbic acid store is essentially free of other added active components.

13. The method as claimed in claim 12 wherein the microbes are fungi or yeasts.

14. The process as claimed in claim 5, wherein the oil is selected from one or more of a branched or unbranched $C_1$–$C_4$-alkanol and $C_2$–$C_4$-alkanediol.

15. The process as claimed in claim 7, wherein the concentration is from 10% by weight to 40% by weight.

16. A process for producing a wood as claimed in claim 1, which comprises
   a) treating wood with a solution of one or more of sorbic acid and a salt of sorbic acid
   b) drying the wood thus treated and
   c) treating the dried wood with a solution containing one or more water-soluble calcium or magnesium salts.

17. A process for producing a wood as claimed in claim 1, which comprises
   a) treating wood with one or more of sorbic acid and a salt of sorbic acid,
   b) drying the wood thus treated and
   c) treating the dried wood with a solution comprising one or more acids selected from formic acid, acetic acid, propionic acid, citric acid, fumaric acid, lactic acid, hydrochloric acid, sulfuric acid and phosphoric acid.

* * * * *